(12) United States Patent
Fujiwara et al.

(10) Patent No.: US 9,277,852 B2
(45) Date of Patent: Mar. 8, 2016

(54) PROBE

(75) Inventors: Katsumi Fujiwara, Hachioji (JP); Hiroyuki Katsurada, Itabashi-ku (JP); Yuichi Atarashi, Hachioji (JP)

(73) Assignee: Konica Minolta Advanced Layers, Inc., Toyko (JP)

( * ) Notice: Subject to any disclaimer, the term of this patent is extended or adjusted under 35 U.S.C. 154(b) by 0 days.

(21) Appl. No.: 13/643,029

(22) PCT Filed: Apr. 19, 2011

(86) PCT No.: PCT/JP2011/059600
§ 371 (c)(1),
(2), (4) Date: Oct. 23, 2012

(87) PCT Pub. No.: WO2011/132661
PCT Pub. Date: Oct. 27, 2011

(65) Prior Publication Data
US 2013/0038872 A1 Feb. 14, 2013

(30) Foreign Application Priority Data

Apr. 23, 2010 (JP) .................................. 2010-099867
Apr. 23, 2010 (JP) .................................. 2010-099868

(51) Int. Cl.
*G01J 3/44* (2006.01)
*A61B 1/00* (2006.01)
(Continued)

(52) U.S. Cl.
CPC ......... *A61B 1/00177* (2013.01); *A61B 1/00179* (2013.01); *A61B 1/00183* (2013.01); *A61B 5/0084* (2013.01); *G01J 3/02* (2013.01); *G01J 3/021* (2013.01); *G01J 3/0218* (2013.01); *G01J 3/0256* (2013.01); *G01J 3/06* (2013.01);
(Continued)

(58) Field of Classification Search
CPC ............. G06T 1/00; A61B 1/05; G02B 23/26
USPC .................................... 356/301; 600/109, 173
See application file for complete search history.

(56) References Cited

U.S. PATENT DOCUMENTS 5,797,836 A * 8/1998 Lucey et al. .................. 600/109
6,428,470 B1 * 8/2002 Thompson .................... 600/173

FOREIGN PATENT DOCUMENTS

JP 63-164932 7/1988
JP 4-341232 11/1992
(Continued)

OTHER PUBLICATIONS

Search Report dated Aug. 23, 2013 issued in the corresponding European Patent Application No. 11 77 1996.3.

*Primary Examiner* — Tarifur Chowdhury
*Assistant Examiner* — Jamil Ahmed
(74) *Attorney, Agent, or Firm* — Cozen O'Connor

(57) ABSTRACT

A probe includes an optical system which irradiates a site of a biological tissue and receives light emitted from the site, and an imaging device. The imaging device is disposed ahead of the optical system closer to the end of the probe. The probe rotates the incident direction of the light and the imaging direction of the imaging device around a rotation axis directed to the longitudinal direction of the probe while fixing an angle between the incident direction and the imaging direction. The optical system receives the light from the site which always falls in the field of view of the imaging device, or brought with a time lag into the field of view of the imaging device as a result of rotation, the light being incident in the direction normal to, or inclined away from the rotation axis.

13 Claims, 20 Drawing Sheets

(51) Int. Cl.
 A61B 5/00 (2006.01)
 G01J 3/02 (2006.01)
 G01J 3/06 (2006.01)
 G01N 21/64 (2006.01)
 G01N 21/65 (2006.01)
 G02B 23/24 (2006.01)
 A61B 1/005 (2006.01)
 A61B 1/04 (2006.01)
 A61B 1/05 (2006.01)
 A61B 1/06 (2006.01)

(52) U.S. Cl.
 CPC ............ *G01N21/6456* (2013.01); *G01N 21/65* (2013.01); *G02B 23/2423* (2013.01); *G02B 23/2469* (2013.01); *A61B 1/0051* (2013.01); *A61B 1/043* (2013.01); *A61B 1/05* (2013.01); *A61B 1/0676* (2013.01); *A61B 5/6853* (2013.01); *G01J 3/4406* (2013.01)

(56) References Cited

FOREIGN PATENT DOCUMENTS

| | | | | |
|---|---|---|---|---|
| JP | 9-294707 | | | 11/1997 |
| JP | 09294707 | A | * | 11/1997 |
| JP | 10-127562 | | | 5/1998 |
| JP | 2001-79007 | | | 3/2001 |
| JP | 2003-204926 | | | 7/2003 |
| JP | 2005-319292 | | | 11/2005 |
| JP | 2006-87447 | | | 4/2006 |
| JP | 2006087447 | A | * | 4/2006 |
| JP | 2008-48787 | | | 3/2008 |

* cited by examiner

PROBE

RELATED APPLICATIONS

This is a U.S. National Phase Application under 35 USC 371 of International Application PCT/JP2011/059600 filed on Apr. 19, 2011.

This application claims the priority of Japanese application no. 2010-099868 filed Apr. 23, 2010 and 2010-099867 filed Apr. 23, 2010, the entire content of both of which are hereby incorporated by reference.

FIELD OF THE INVENTION

The present invention relates to a probe which includes an optical system which irradiates a site of a biological tissue to be observed with irradiation light and receives emission light caused by the irradiation light and emitted from the site; and an imaging device which captures a surface image of the site.

DESCRIPTION OF RELATED ART

There has been developed a probe configured to irradiate light such as excited light onto a site of a biological tissue to be observed, and to detect emission light such as fluorescent light caused by the irradiation light and emitted from the biological tissue or from a chemical preliminarily injected into the biological body. The probe has been used for diagnosing degeneration of the biological tissue or state of cancer (for example, types of disease, and range of infiltration).

This sort of probe is equipped with optical parts such as an optical fiber which irradiates light to the site of biological body to be observed, and receives light emitted from a lesion. In order to satisfy a need for visually confirming the periphery of the site, there has also been proposed a probe further equipped with an imaging device for capturing image of the site.

Patent Documents 1 and 2 describe probes each having optical parts for irradiating excited light onto a site of biological body to be observed and receiving reflected light from a lesion; and an imaging device for capturing a surface image of the site.

According to the probe described in Patent Document 1, direction of observation of fluorescent light and direction of imaging are aligned in the direction pointed by the end of the probe, the reflected light from the site is received through the same light path, and then split by a beam splitter for detection of fluorescence and imaging.

In each of the probes described in Patent Documents 1 and 2, an optical system for irradiating the excited light onto the site of biological body to be observed and receiving the reflected light from the site, and the imaging device are aligned in the radial direction of the probe, and thereby both of the direction of observation of fluorescent light and the direction of imaging are the direction pointed by the end of the probe.

In a probe described in Patent Document 3, the direction of observation of fluorescent light is directed to the side of the probe, and the direction of imaging is the direction pointed by the end of the probe.

On the other hand, in a probe described in Patent Document 4, the excited light scans the site of biological body to be observed in the circumferential direction and the longitudinal direction, and a plurality of photo-detectors are arranged in a circumferential manner so as to receive the fluorescent light caused by the excited light and emitted from the site.

PRIOR ART DOCUMENTS

Patent Documents

Patent Document 1: Japanese Laid-Open Patent Publication No. H09-294707
Patent Document 2: Japanese Laid-Open Patent Publication No. 2005-319212
Patent Document 3: Japanese Laid-Open Patent Publication No. 2008-48787
Patent Document 4: Japanese Laid-Open Patent Publication No. H10-127562

SUMMARY

Problems to be Solved by the Invention

Problems have, however, remained in the prior art described in the above.

The probes described in Patent Documents 1 and 2 have the optical system for irradiating the excited light onto the site of biological body to be observed and receiving the reflected light from the site, and the imaging device are aligned in the radial direction of the probe, and both of the direction of observation of the fluorescent light and the direction of imaging are the direction pointed by the end of the probe.

It is therefore difficult to reduce the diameter of the probe, and to capture image or to observe fluorescent light on the side of the probe.

With the probes described in Patent Documents 1, 2 and 3, it is difficult to capture image on the side of the probe, and there is no means for rotational scanning around the axis which extends in the longitudinal direction of the probe.

The probe described in Patent Document 4 has no imaging device for capturing a surface image of the site, besides the optical receiver for receiving the fluorescent light. Thus, the site cannot be visually observed in the probe of Patent Document 4.

The present invention is conceived considering the problems in the prior art, and a subject thereof is to provide a probe which includes an optical system which irradiates a site of a biological tissue to be observed with irradiation light, and receives emission light emitted from the site; and an imaging device which captures a surface image of the site, aiming at reducing the diameter of the probe, facilitating capture of image or observation of emission light on the side of the probe, so as to benefit diagnosis.

In addition, the present invention is also conceived considering the problems in the prior art, and another subject thereof is to provide a probe which includes an optical system which irradiates a site of a biological tissue to be observed with irradiation light, and receives emission light emitted from the site; and an imaging device which captures a surface image of the site, aiming at obtaining intensity distribution information of emitted light obtainable by scanning in the receiving direction of emission light and the direction of imaging, in the form overlaid with image information expressed on the same coordinate, so as to benefit diagnosis.

Means for Solving the Problems

Aimed at solving the above-described problems, according to the invention of embodiment 1, there is provided a probe which includes an optical system which irradiates a site of a biological tissue to be observed with irradiation light and receives emission light emitted from the site; and an imaging device which captures a surface image of the site.

The imaging device is disposed ahead of the optical system, closer to the end of the probe.

According to the invention of embodiment 2, there is provided the probe of embodiment 1, wherein the optical system includes: an irradiating optical fiber for irradiating the irradiation light; a receiving optical fiber for receiving the emission light; and an optical element disposed ahead of the irradiating optical fiber and the receiving optical fiber, closer to the end of the probe, and having a reflective surface in a light path of the emission light, so as to allow the receiving optical fiber to receive the emission light coming into the probe in the direction normal to, or inclined away from, the longitudinal direction of the probe.

According to the invention of embodiment 3, there is provided the probe of embodiments 1 or 2, wherein view angle of the imaging device contains the direction normal to the direction pointed by the end of the probe.

According to the invention of embodiment 4, there is provided the probe of embodiment 3, wherein view angle of the imaging device contains the direction pointed by the end of the probe.

According to the invention of embodiment 5, there is provided the probe of embodiments 3 or 4, wherein field of view of the imaging device contains a region on the outer surface of the probe where the irradiation light and the emission light pass through.

According to the invention of embodiment 6, there is provided the probe of embodiments 1 to 5, wherein the optical system receives fluorescent light, scattered light or Raman scattered light caused by the irradiation light.

According to the invention of embodiment 7, there is provided a probe which includes an optical system which irradiates a site of a biological tissue to be observed with irradiation light and receives emission light emitted from the site to be observed; and an imaging device which captures a surface image of the site to be observed.

The probe is configured to rotate the direction of incidence of the emission light to be received on the probe and the direction of imaging of the imaging device around an axis of rotation which extends in the longitudinal direction of the probe while fixing an angle between the direction of incidence and the direction of imaging.

According to the invention of embodiment 8, there is provided the probe of embodiment 7, wherein an optical element which determines the direction of incidence of the emission light on the probe, and the imaging device are attached to a unit.

The probe further comprises a rotating section rotating the unit around the axis of rotation.

According to the invention of embodiment 9, there is provided the probe of embodiments 7 or 8, configured to receive the emission light incident on the probe in the direction normal to, or inclined away from, the axis of rotation.

According to the invention of embodiment 10, there is provided the probe of embodiment 9, configured to receive the emission light emitted from the site to be observed, which always falls in the field of view of the imaging device, or brought with a time lag into the field of view of the imaging device as a result of rotation.

According to the invention of embodiment 11, there is provided the probe of embodiment 10, configured to receive the emission light emitted from the site to be observed, which always falls in the field of view of the imaging device, or brought with a time lag into the field of view of the imaging device as a result of rotation, by adjusting the direction of incidence more largely inclined towards the field of view of the imaging device, away from the direction normal to the axis of rotation.

According to the invention of embodiment 12, there is provided the probe of claim 9, configured to receive the emission light emitted from the site to be observed, which always falls outside the field of view of the imaging device, and brought with a time lag into the field of view of the imaging device as a result of rotation.

According to the invention of embodiment 13, there is provided the probe of embodiment 12, configured to receive the emission light emitted from the site to be observed, which always falls outside the field of view of the imaging device, and brought with a time lag into the field of view of the imaging device as a result of rotation, by ensuring a relative angle to the view angle of the imaging device between the direction of incidence and the axis of rotation.

According to the invention of embodiment 14, there is provided the probe described in any one of embodiments 7 to 13, wherein view angle of the imaging device contains the direction normal to the axis of rotation.

According to the invention of embodiment 15, there is provided the probe of embodiment 14, wherein view angle of the imaging device contains the direction pointed by the end of the probe.

According to the invention of embodiment 16, there is provided the probe of embodiments 14 or 15, wherein field of view of the imaging device contains a region on the outer surface of the probe where the irradiation light and the emission light pass through.

According to the invention of embodiment 17, there is provided the probe described in any one of embodiments 7 to 16, wherein the optical system receives fluorescent light, scattered light or Raman scattered light caused by the irradiation light.

According to the invention of embodiment 18, there is provided a probe which includes an optical system which irradiates a site of a biological tissue to be observed with irradiation light, and receives emission light emitted from the site; and an imaging device which captures a surface image of the site.

The imaging device is disposed ahead of the optical system, closer to the end of the probe.

The probe is configured to rotate the direction of incidence of the emission light to be received on the probe and the direction of imaging of the imaging device around an axis of rotation which extends in the longitudinal direction of the probe while fixing an angle between the direction of incidence and the direction of imaging.

Effects of the Invention

According to the invention described in any one of embodiments 1 to 6, since the imaging device is disposed ahead of the optical system, which irradiates the irradiation light onto the site of the biological tissue to be observed and receives the emission light from the site, closer to the end of the probe, the optical system and the imaging device are not aligned in the radial direction of the probe. Also since a cable for transmitting image signal from the imaging device may be routed while avoiding the optical system, the probe may be reduced in the diameter, the optical system and the imaging device may be aligned in the direction of axis which extends in the longitudinal direction of the probe, which facilitates imaging and observation of the emission light on the side of the probe, and benefits diagnosis.

Also since the imaging device is disposed on the end side of the probe, the imaging in the direction pointed by the end of the probe may be facilitated.

According to the invention described in any one of embodiments 7 to 17, the angle between the direction of incidence of emission light emitted from the site of the biological tissue and the direction of imaging of the imaging device is kept constant even during scanning under rotation around the axis of rotation, and the angle may be specified. Therefore, intensity distribution information of emitted light obtainable by scanning in the receiving direction of emission light and the direction of imaging, and image information may be acquired as an overlaid image expressed on the same coordinate. This benefits diagnosis.

DESCRIPTION OF THE PREFERRED EMBODIMENTS

An embodiment of the present invention will be explained referring to the attached drawings, merely as one embodiment of the present invention, without limiting the present invention.

Figure 1A:
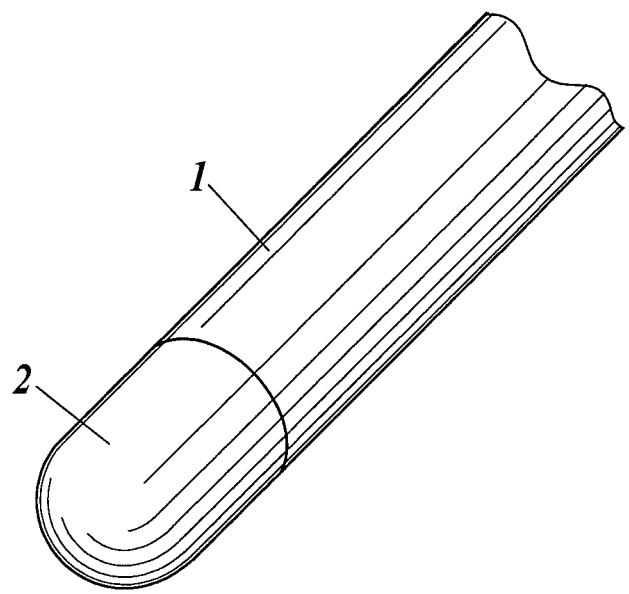
FIG. 1A is a perspective view of an appearance of a probe according to one embodiment of the present invention.

An appearance of the probe of this embodiment is illustrated in FIG. 1A. The probe is basically configured by a bendable tube 1, and an end sheath 2. An opening at the top of the tube 1 and an opening at the bottom of the end sheath 2 are joined and sealed liquid-tightly. The end sheath 2 has a shape composed of a hemispherical dome-like end portion and a circular cylinder connected to the end portion. The end sheath 2 is composed of a molding resin or the like. The end sheath 2 is transparent in the entire portion thereof, or only in a portion thereof.

Figure 1B:
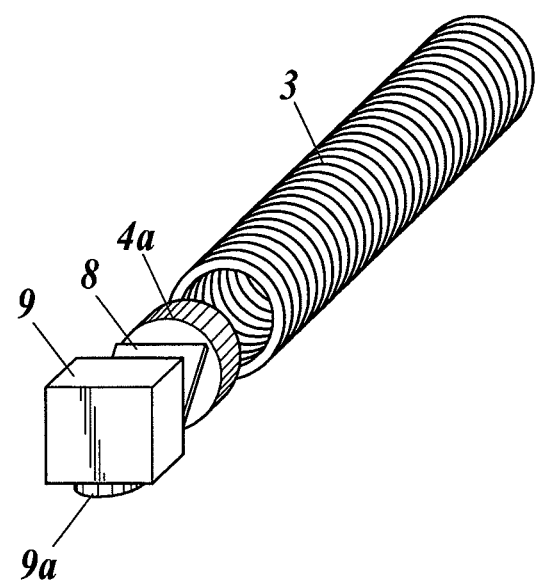
FIG. 1B is a perspective view of an internal configuration of the probe according to one embodiment of the present invention.
Figure 1C:
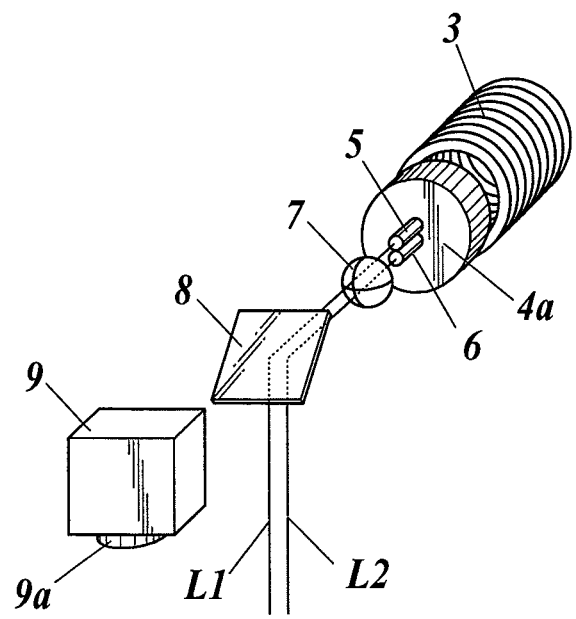
FIG. 1C is an exploded perspective view of an internal configuration of a probe according to one embodiment of the present invention.

FIG. 1A, FIG. 1B and FIG. 1C illustrate an internal configuration of the probe. Configured in the tube 1 are a torque coil 3, a unit frame base 4a, an irradiating optical fiber 5, a receiving optical fiber 6, a condenser lens 7, a minor (or prism, the same will apply hereinbelow) 8, and an imaging camera 9. A component schematically illustrated with reference numeral 9a is a lens unit of the imaging camera 9. The torque coil 3 extends to reach the base end of the tube 1, and is rotated at the base end by an actuator such as servo motor.

The unit frame base 4a is formed into a disk shape, and is fixed to the end of the torque coil 3. The unit frame base 4a holds the irradiating optical fiber 5 and the receiving optical fiber 6. A unit frame has an unillustrated side wall which extends from the circumference of the unit frame base 4a, so as to hold therein the condenser lens 7, the mirror 8 and the imaging camera 9. The entire portion of the unit frame rotates as the torque coil rotates.

Axes of the irradiating optical fiber 5 and the receiving optical fiber 6 are directed to the end of the probe, and ahead of them closer to the end, the condenser lens 7, the mirror 8 and the imaging camera 9 are disposed in this order as viewed from the optical fiber side. The imaging camera 9 is also equipped with an unillustrated lighting device used for imaging.

More specifically, the imaging device is disposed on the end side of the probe, ahead of the optical system which irradiates the excited light onto the site of the biological tissue to be observed, and receives the reflected light from the site. It is very difficult to divert the irradiating optical fiber 5 and receiving optical fiber 6 from the imaging camera 9 without disposing the imaging camera 9 on the end side. Now by disposing the imaging camera 9 on the end side, the imaging camera 9 may be disposed nearly coaxially with the optical system composed of the irradiating optical fiber 5, the receiving optical fiber 6, the condenser lens 7 and the mirror 8, and thereby the probe may be reduced in diameter. Disposition of the imaging camera 9 on the end side also facilitates imaging in the direction pointed by the end of the probe.

The base end of the probe is connected to an unillustrated base unit. On the base unit, configured are a light source of the excited light, a spectrometer, an image processor, the actuator and so forth. The torque coil 3 is connected to the actuator, the base end of the irradiating optical fiber 5 is connected to the light source, the base end of the receiving optical fiber 6 is connected to the spectrometer, and an unillustrated signal transmission cable of the imaging camera 9 is connected to the image processor.

Figure 2:
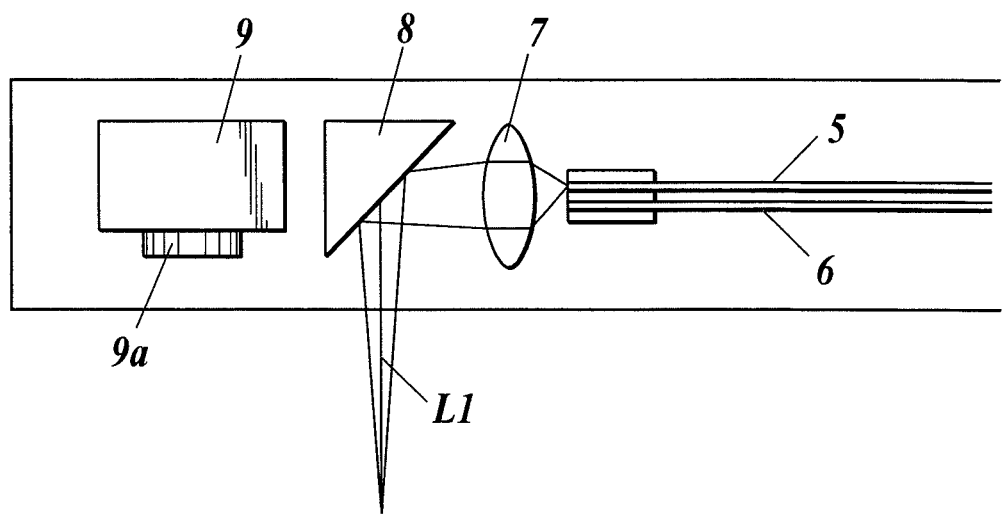
FIG. 2 is a schematic side elevation illustrating a layout of internal constituents of the probe according to one embodiment of the present invention.

As illustrated in FIG. 2, the excited light emitted from the irradiating optical fiber 5 is condensed by the condenser lens 7, reflected on the mirror 8 to be directed sidewards, and irradiated onto the site of the biological tissue to be observed. In the site, fluorescent light is caused by the excited light depending on the state of lesion. The thus-generated light containing fluorescent light enters the mirror 8 and reflected thereon, condensed by the condenser lens 7, and enters the receiving optical fiber 6. The light guided through the receiving optical fiber 6 is input into the spectrometer in the base unit. The fluorescent light in the broad sense is an electromagnetic wave emitted when an object irradiated by X ray, ultraviolet radiation or visible light absorbs the energy to excite electrons thereof, and then releases excessive energy when the electrons fall down to the ground state. Since the fluorescent light is obtained herein as an optical feedback caused by the excited light (reference light) but different therefrom in the wavelength, it is guided through the receiving optical fiber 6 into the spectrometer in the base unit to be analyzed for spectral distribution, based on which the lesion of the site may be detected.

The imaging camera 9 is equipped with an imaging element such as CCD, C-MOS image sensor or the like for capturing the surface image of the site to be observed.

Figure 3A:
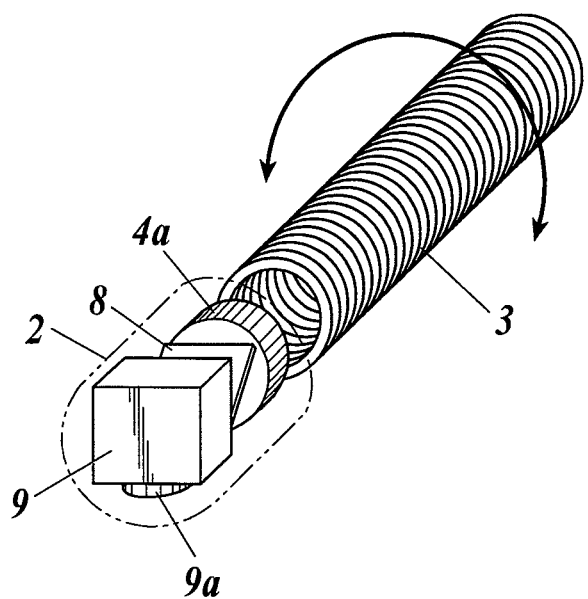
FIG. 3A is a perspective view of an internal configuration of the probe according to one embodiment of the present invention.
Figure 3B:
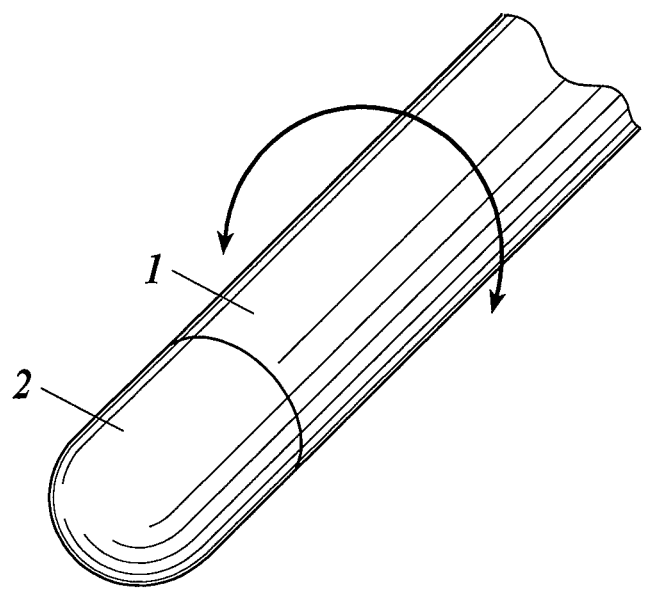
FIG. 3B is a perspective view of an appearance of the probe according to one embodiment of the present invention.

The probe may be configured so that only the internal constituents are rotatable as illustrated in FIG. 3A, or so that the entire body including the exterior constituent and the internal constituents are rotatable together as illustrated in FIG. 3B. In the former case, the entire portion of the end sheath 2 is preferably transparent. Parts of the end sheath 2 other than the output region of the excited light, the input region of the reflected light, and the region of the field of view of the imaging camera 9, are not necessarily transparent. In the latter case, it suffices that the end sheath 2 is transparent at least in the output region of the excited light, the input region of the reflected light, and the region of the field of view of the imaging camera 9.

Figure 4A:
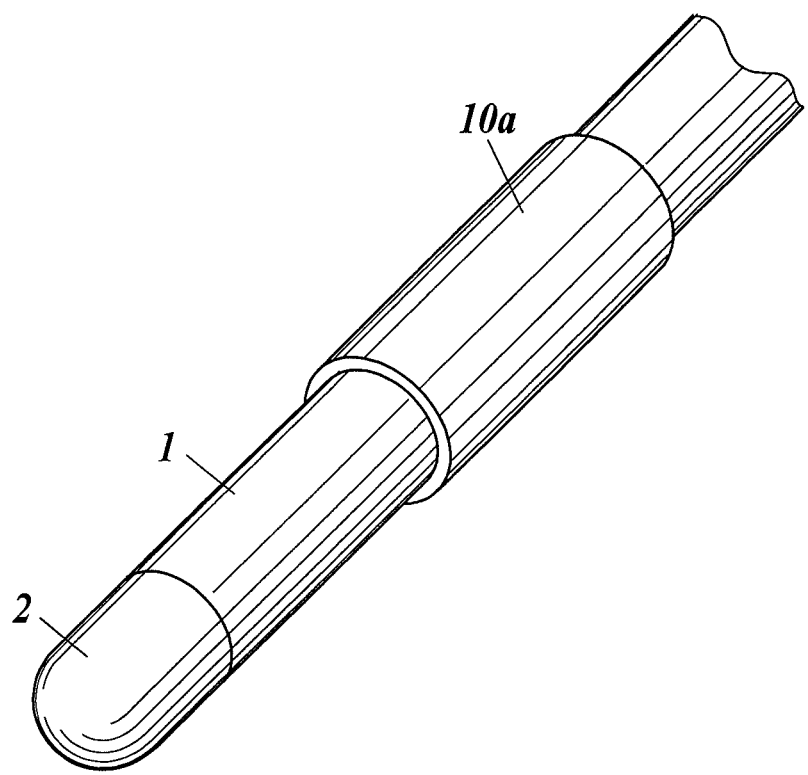
FIG. 4A is a perspective view of an appearance of the probe attached with a balloon according to one embodiment of the present invention, with the balloon shrunk.
Figure 4B:
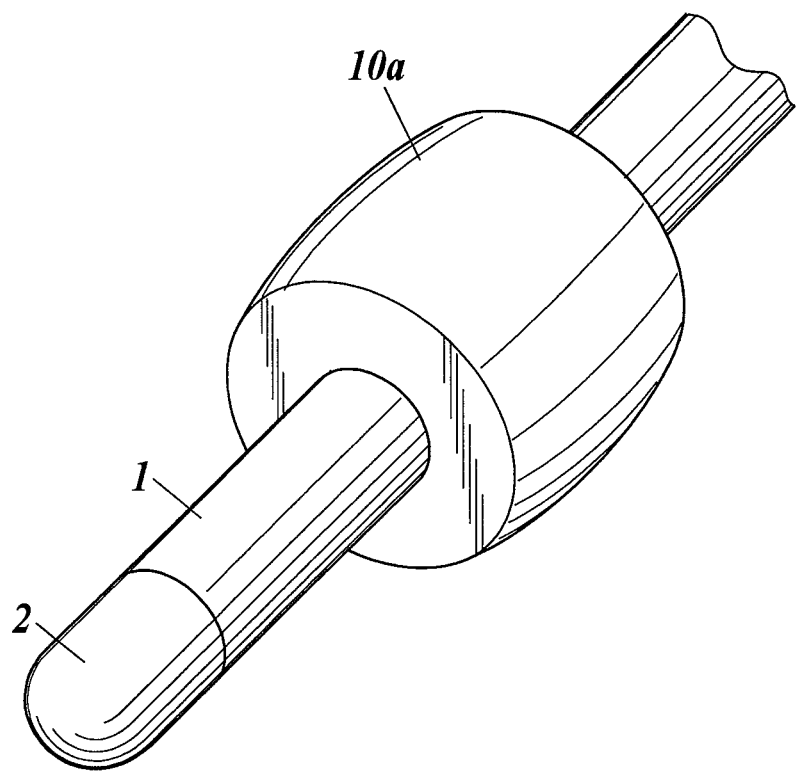
FIG. 4B is a perspective view of an appearance of the probe attached with the balloon according to one embodiment of the present invention, with the balloon swelled.

For example when the unit frame is rotated, it is effective to immobilize the probe making use of a configuration such as allowing a balloon 10a, which is provided as a probe immobilizing device as illustrated in FIGS. 4A and 4B, to swell so as to bring it into contact with the inner wall of lumen.

A mechanism for rotating the probe and an immobilizing mechanism using the balloon 10a will be explained referring to FIGS. 5A, 5B, 5C and 5D.

As illustrated in FIGS. 5A, 5B, 5C and 5D, the unit frame 4 is formed into a cylindrical shape. Inside the unit frame 4, fixed are the condenser lens 7, the mirror 8 and the imaging camera 9, so as to configure a rotating unit M. A window 4b is provided to the circumferential surface of the unit frame 4. The window 4b is configured by a transparent component, or an opening. The window 4b is provided for the convenience of output of the excited light, input of the reflected light, output of lighting beam which assists imaging by the imaging camera 9, and imaging by the imaging camera 9. Axis X indicates the axis of rotation which is directed to the longitudinal direction of the probe.

Figure 5A:
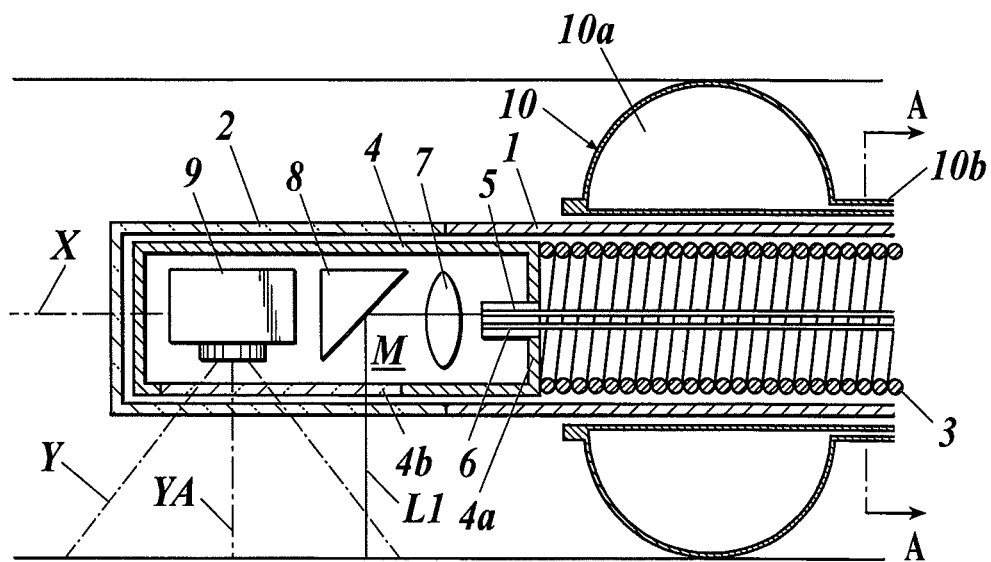
FIG. 5A is a vertical cross sectional view of the probe according to one embodiment of the present invention.
Figure 5B:
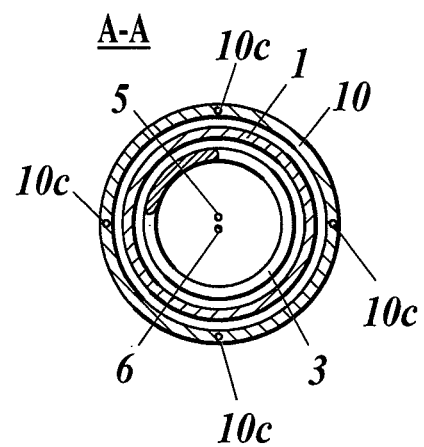
FIG. 5B is a transverse cross sectional view of the probe according to one embodiment of the present invention.

In the configuration illustrated in FIGS. 5A and 5B, the entire portion of the end sheath 2 is transparent. A motive power transmitted through the torque coil 3 rotates the rotating unit M in the end sheath 2 around the axis of rotation X.

Figure 5C:
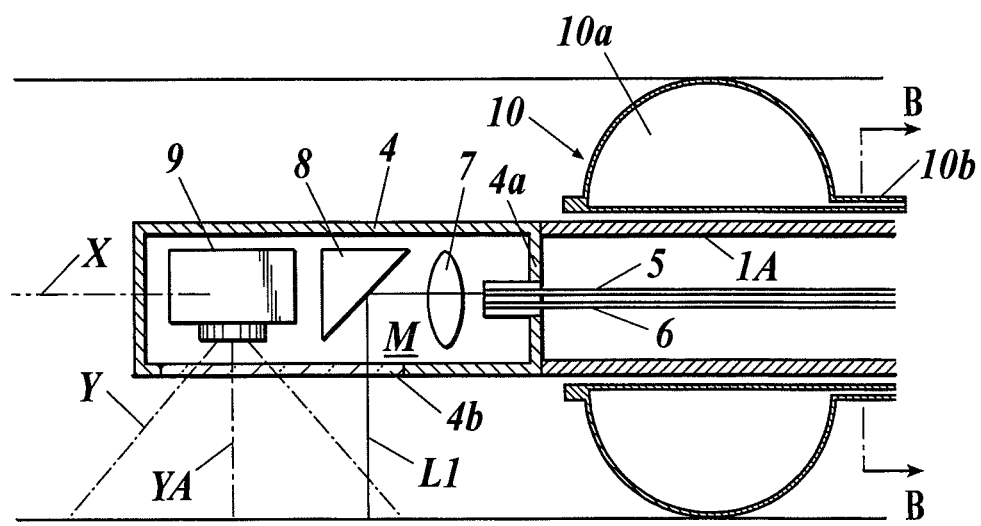
FIG. 5C is a vertical cross sectional view of a probe according to another embodiment of the present invention.
Figure 5D:
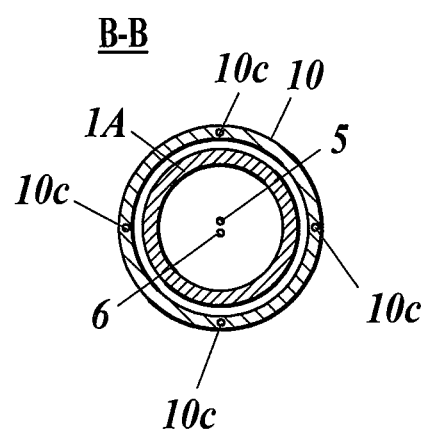
FIG. 5D is a transverse cross sectional view of a probe according to another embodiment of the present invention.

In the configuration illustrated in FIGS. 5C and 5D, the unit frame 4 also serves as the end sheath. The window 4b is therefore configured by a transparent component, rather than an opening. In the configuration illustrated in FIGS. 5C and 5D, the unit frame 4 is connected to a torque tube 1A through which the torque may be transmitted, and the base end of the torque tube 1A is connected to the actuator, thereby the rotating unit M rotates around the axis of rotation X, with the aid of the motive power transmitted through the torque tube 1A. The torque tube 1A is typically configured by a tube covering a torque coil.

In either configuration, the entire portion may be transparent, rather than providing the window 4b in a specified region.

Since the rotating unit M is connected with the optical fibers 5, 6, the rotating unit M is designed to rotate within a restricted angle of rotation. Also the rotational scanning described later is proceeded so as to be inverted at a predetermined angle of rotation (for example, when the motion reaches 360°, or exceeds 360°).

The above-described detection of fluorescent light and imaging through the imaging camera 9 are conducted under rotational scanning by the rotating unit M, so as to obtain intensity distribution information of fluorescent light and image information. The information are stored in a memory mounted on the base unit. In this configuration, the direction of incidence into the probe of the reflected light is determined by the mirror 8. The reflected light is received and detected by the probe after being reflected on the site irradiated by the excited light emitted from the probe. The angle between the direction of incidence of the reflected light and the direction of imaging of the imaging camera 9 is kept constant during the rotational scanning and may be specified. By preliminarily setting the angle as a constant into an information processing device, intensity distribution information of fluorescent light and image information may be output on a display as an overlaid image expressed on the same coordinate.

The balloon 10a is formed as a part of the outer tube 10. The outer tube 10 is a multi-lumen tube having holes 10c running throughout a skin 10b in the longitudinal direction, wherein the holes 10c communicate with the inner space of the balloon 10a so as to form the inner space in the skin. Base ends of the holes 10c are connected to an air pump, so as to allow therethrough feeding and sucking of air, to thereby expand or shrink the balloon 10a.

During the rotational scanning of the rotating unit M for acquiring the intensity distribution information of fluorescent light and the image information, the balloon 10a is swelled to immobilize the axis of rotation X of the rotating unit M. The probe as a whole, containing the rotating unit M, is movable in the axial direction with respect to the outer tube 10, so as to enable continuous scanning also in the direction of axis X.

Figure 6A:
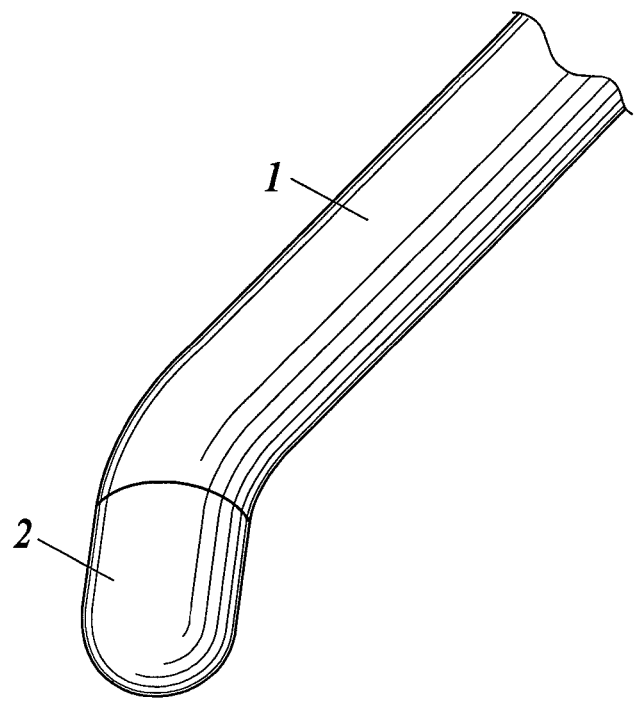
FIG. 6A is a perspective view illustrating an appearance of the probe in a bent state according to one embodiment of the present invention.
Figure 6B:
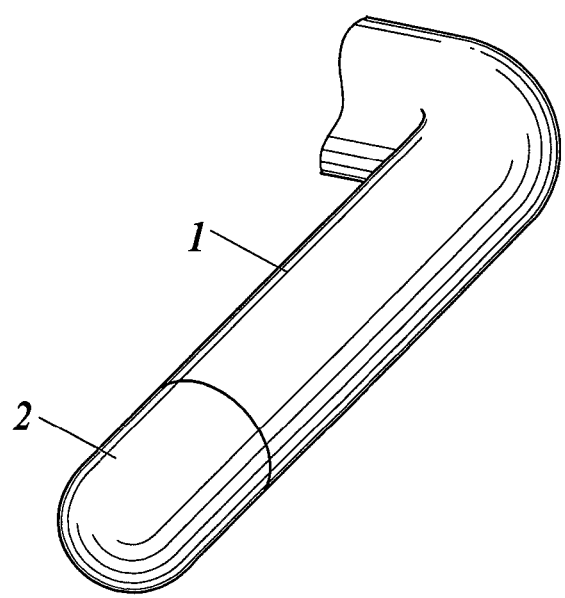
FIG. 6B is a perspective view illustrating an appearance of the probe in a bent state according to one embodiment of the present invention.
Figure 6C:
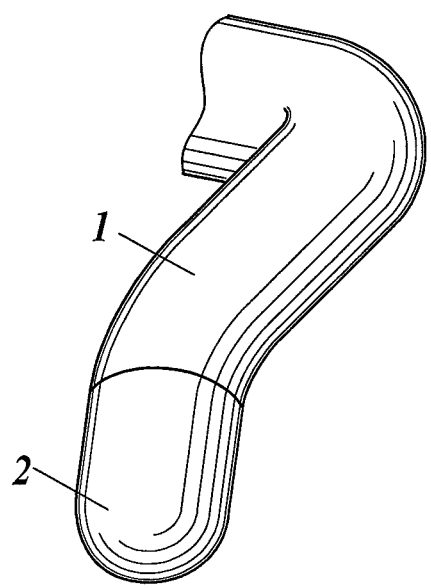
FIG. 6C is a perspective view illustrating an appearance of the probe in a bent state according to one embodiment of the present invention.

Since the probe has a compact design with the rotating unit M encapsulated in the end portion thereof, the probe may be bent in various ways as illustrated in FIGS. 6A, 6B and 6C, such as bent only in the end portion (FIG. 6A), such as bent only in the intermediate portion (FIG. 6B), and such as bent in the end portion and the intermediate portion (FIG. 6C). The probe may therefore be inserted through a nostril or mouth into body, smoothly advances through lumen in the body, and may rotate the rotating unit in the bent state.

Next, relation of the direction of output of the excited light and the direction of incidence of the reflected light, and the field of view of the imaging camera will be explained.

Figure 7A:
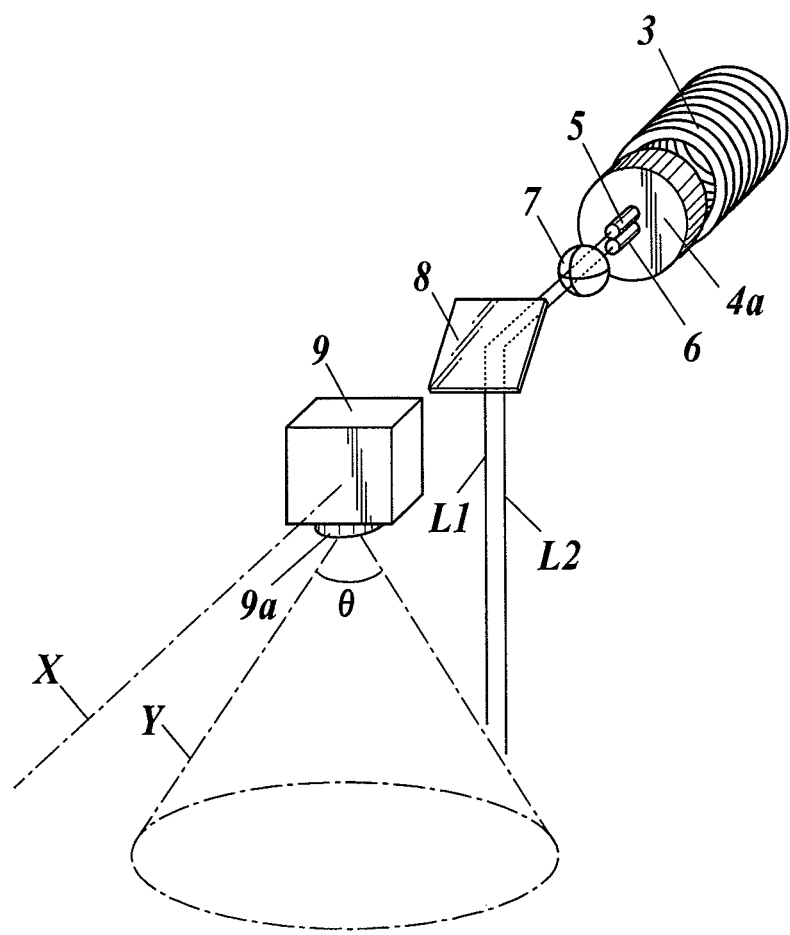
FIG. 7A is an exploded perspective view of an internal configuration of the probe according to one embodiment of the present invention.
Figure 7B:
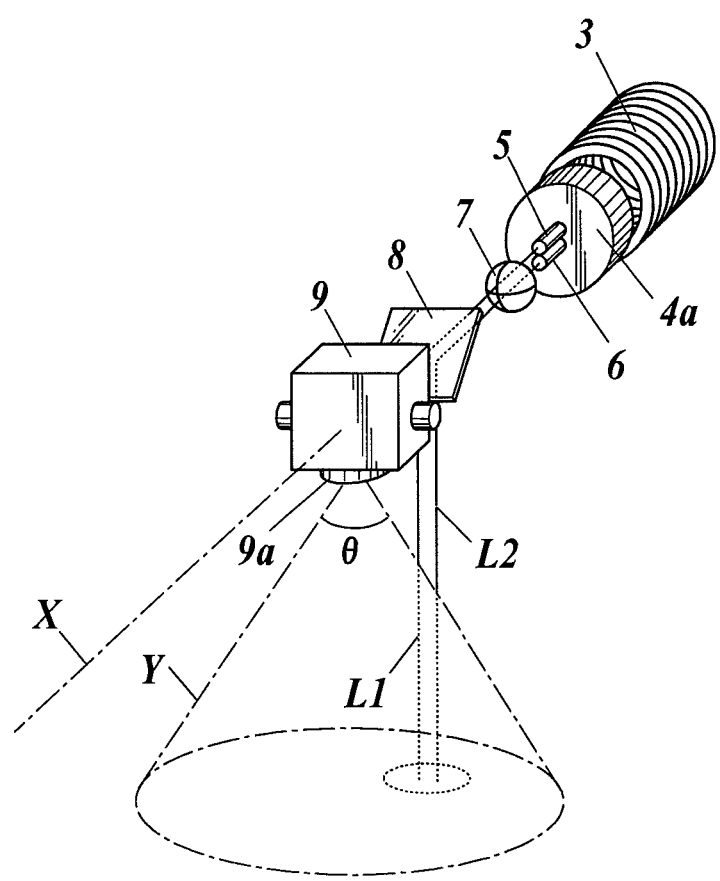
FIG. 7B is an exploded perspective view of an internal configuration of the probe according to one embodiment of the present invention.
Figure 8A:
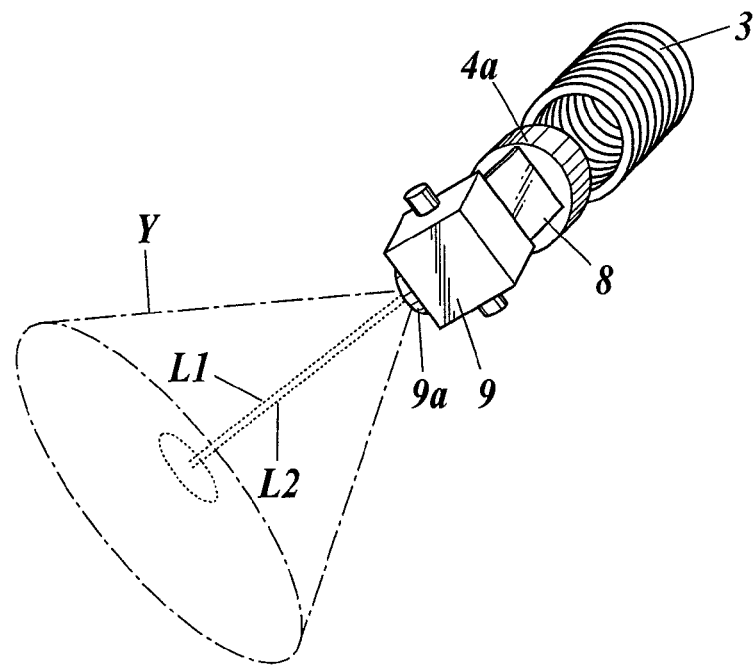
FIG. 8A is a perspective view illustrating an internal configuration of the probe in a rotating state according to one embodiment of the present invention.
Figure 8B:
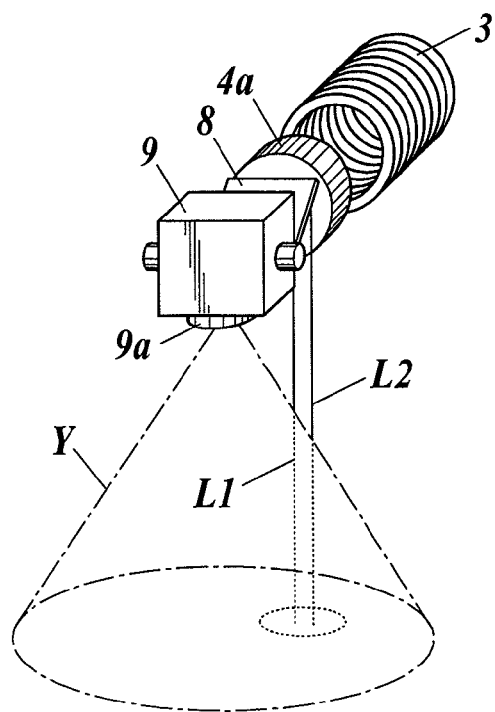
FIG. 8B is a perspective view illustrating the internal configuration of the probe in a rotating state according to one embodiment of the present invention.
Figure 8C:
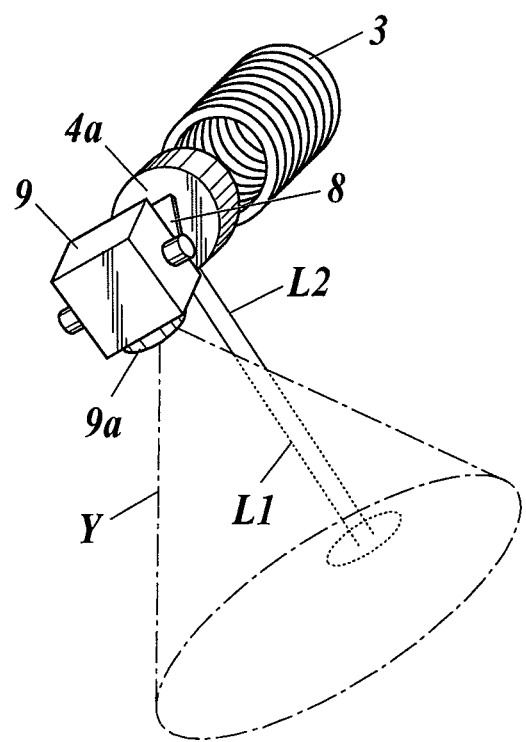
FIG. 8C is a perspective view illustrating the internal configuration of the probe in a rotating state according to one embodiment of the present invention.
Figure 12A:
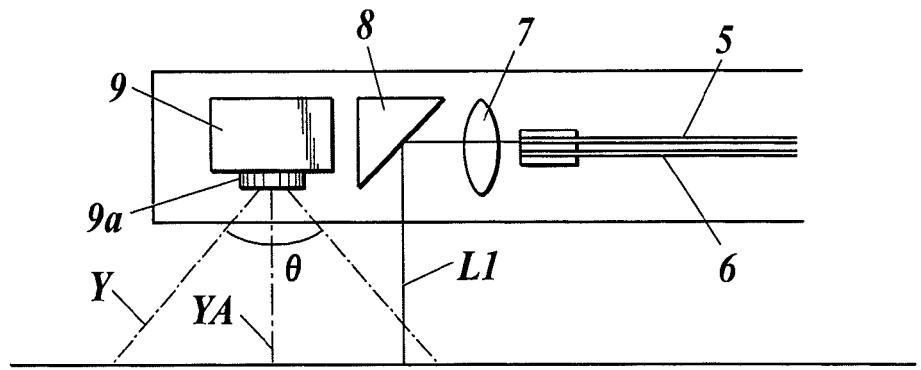
FIG. 12A is a schematic side elevation illustrating a layout of the internal constituents of the probe according to one of the embodiments of the present invention.

In the configuration illustrated in the exploded perspective views in FIGS. 7A and 7B, an emission light path L1 of the excited light and an incident light path L2 of the reflected light are normal to the axis of rotation X of the probe, and directed to the same direction with the field of view Y of the imaging camera 9. While FIG. 7A illustrates the mirror 8 and the imaging camera 9 kept apart from each other, FIG. 7B illustrates the mirror 8 and the imaging camera 9 kept in an actual distance when mounted on the rotating unit M, wherein the site based on detection of fluorescent light falls in the field of view Y. The rotational scanning is implemented as illustrated in FIGS. 8A, 8B and 8C. A layout of this configuration was illustrated in FIG. 12A.

Figure 9A:
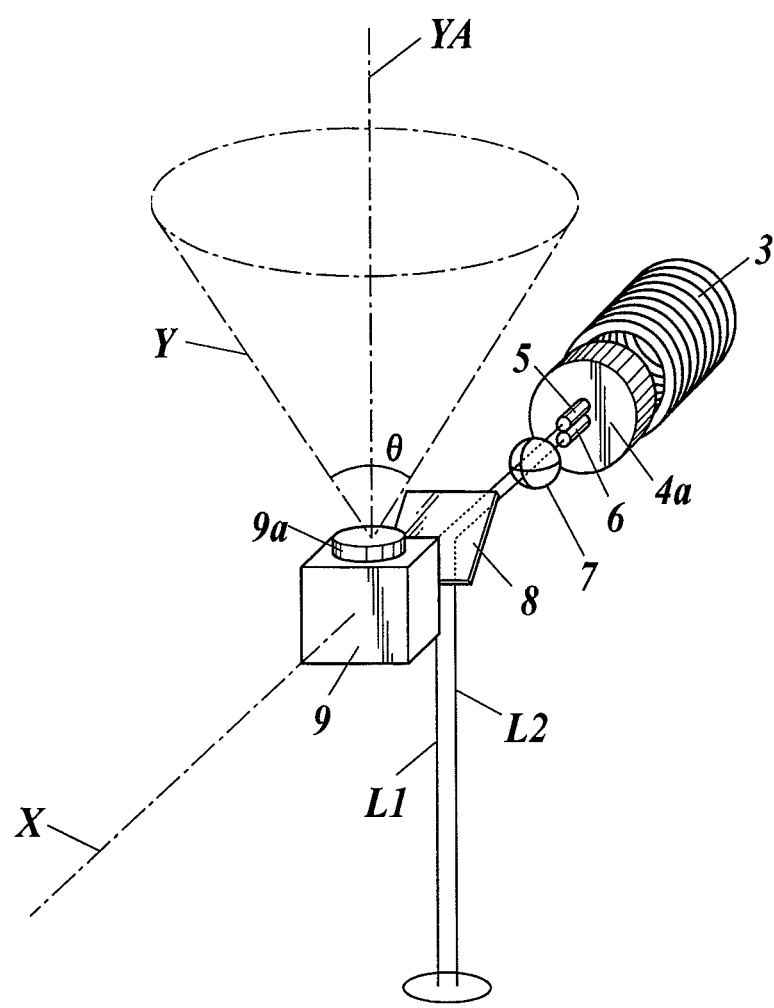
FIG. 9A is an exploded perspective view of an internal configuration of a probe according to another embodiment of the present invention.
Figure 9B:
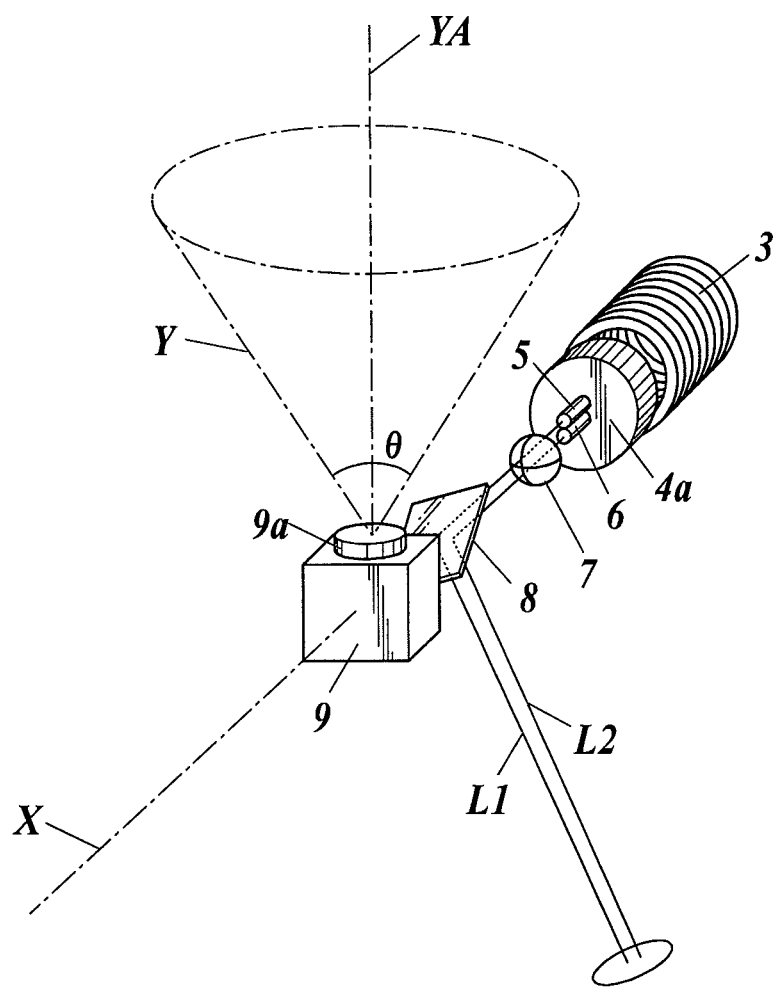
FIG. 9B is an exploded perspective view of the internal configuration of the probe according to another embodiment of the present invention.

FIGS. 9A and 9B also illustrate the mirror 8 and the imaging camera 9 kept in an actual distance when they are mounted on the rotating unit M. In the configuration illustrated in FIGS. 9A and 9B, the emission light path L1 of the excited light and the incident light path L2 of the reflected light are normal to the axis of rotation X.

In the configuration illustrated in FIG. 9A, the emission light path L1 of the excited light and the incident light path L2 of the reflected light are 180° away from the center of field of view YA of the imaging camera 9.

In the configuration illustrated in FIG. 9B, the emission light path L1 of the excited light and the incident light path L2 of the reflected light are inclined away from the axial line which lies at the center of field of view YA of the imaging camera 9.

In short, in either configuration illustrated in FIG. 9A or 9B, the direction of incidence of the reflected light has a relative angle to the view angle θ of the imaging camera 9 between the direction of incidence and the axis of rotation X of the rotating unit M. The expression "a relative angle to the view angle θ" means that the direction of incidence of the reflected light is not contained in the range of view angle θ. Accordingly, the site based on the detection of fluorescent light falls outside the field of view Y, and is brought with a time lag into the field of view Y as the rotating unit M rotates.

With this configuration, if the image information is first acquired and stored in the process of rotational scanning, and next the intensity distribution information of fluorescent light in the already-captured site to be observed is acquired, a visual output of a synthesized result of both information would make an inspector feel discomfort, due to delay of the output image from the real-time captured image.

It is therefore preferable in this configuration to first acquire and store the intensity distribution information of fluorescent light, and next to acquire the image information of the site already went through the measurement of fluorescent light, followed by synthesis of both information. This benefits the inspector since the output image will have only a small time lag behind the real-time image and causes no discomfort.

On the other hand, if the angle between the mirror 8 and the imaging camera 9 is made selectable as illustrated in FIGS. 9A and 9B, the both may be positioned so that a cable led out from the imaging camera 9 does not interfere with the mirror 8. The mirror 8 and the imaging camera 9 may therefore be positioned more closely, and thereby the rotating unit M may advantageously be shortened and downsized.

In the configurations described in the above, the view angle θ of the imaging camera 9 contains the direction normal to the axis X. In the configurations illustrated in FIGS. 10A, 10B and FIGS. 11A and 11B, the view angle θ of the imaging camera 9 contains the direction pointed by the end of the probe. Accordingly, it is now possible to capture an image of the site on the side of the probe, and of the site ahead of the probe, so that the inspector can forward the probe while monitoring the field ahead of the probe on a display.

Figure 10A:
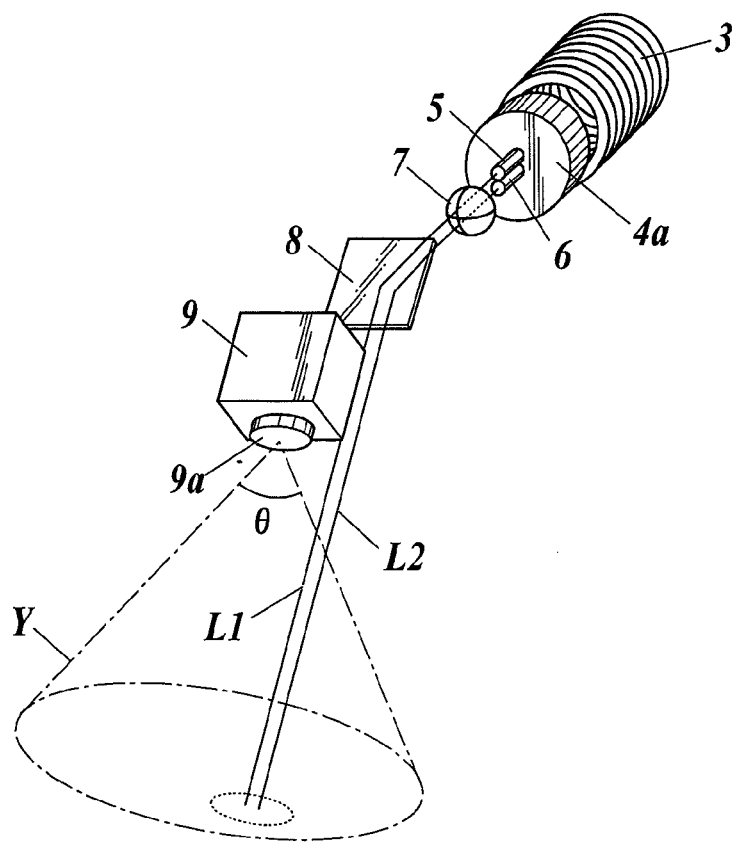
FIG. 10A is an exploded perspective view of the internal configuration of a probe according to another embodiment of the present invention.
Figure 10B:
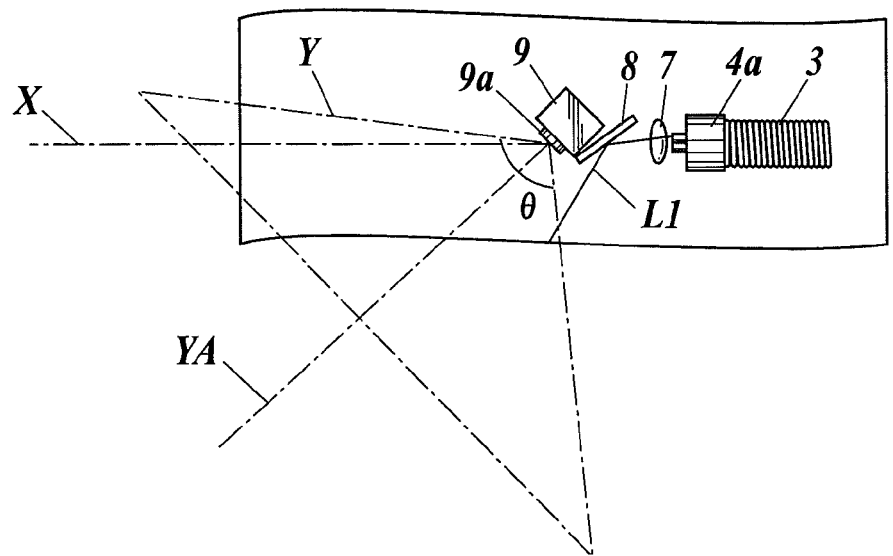
FIG. 10B is a schematic side elevation of the probe according to another embodiment of the present invention.
Figure 11A:
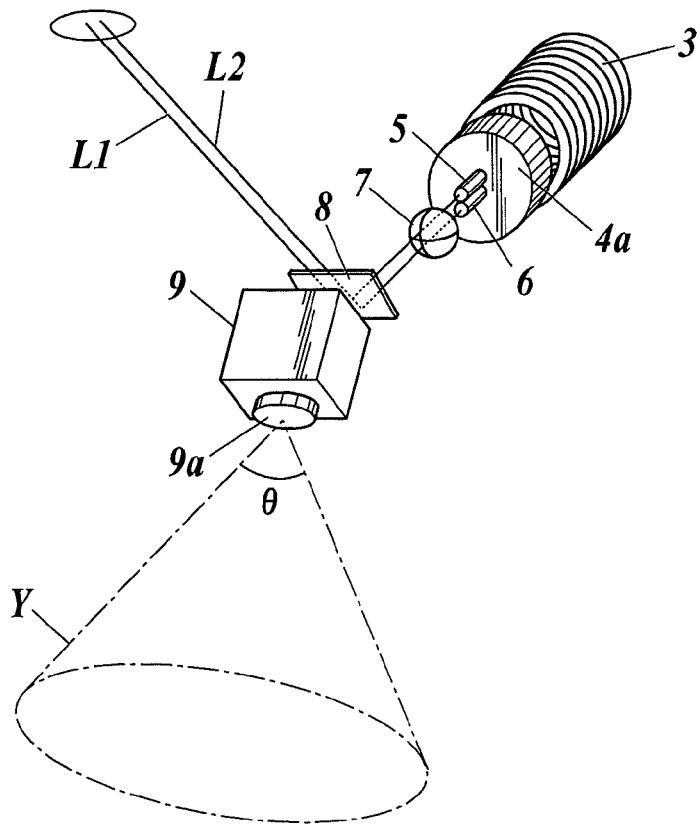
FIG. 11A is an exploded perspective view of an internal configuration of a probe according to another embodiment of the present invention.
Figure 11B:
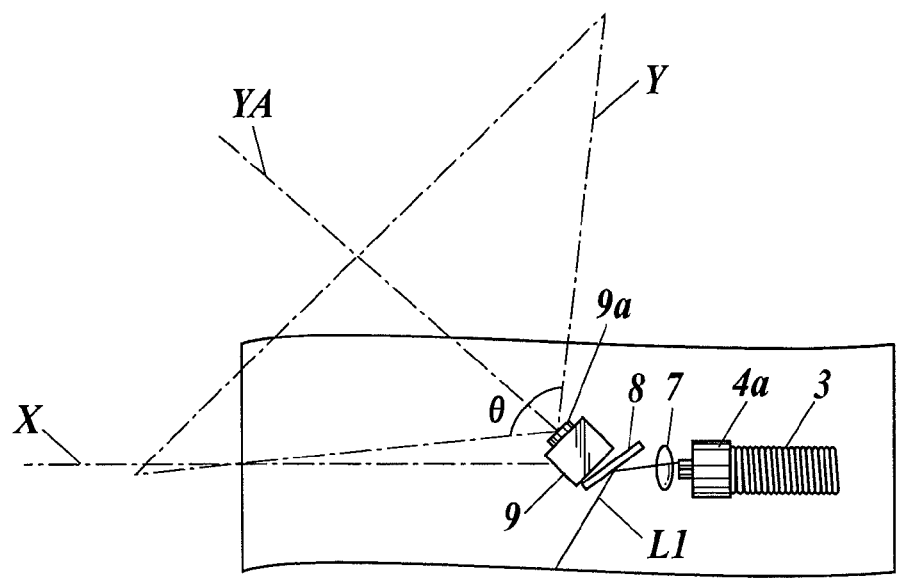
FIG. 11B is a schematic side elevation of the probe according to another embodiment of the present invention.
Figure 12B:
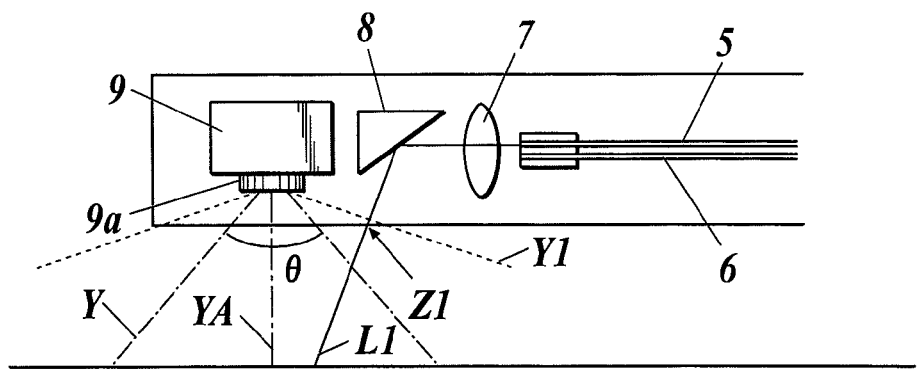
FIG. 12B is a schematic side elevation illustrating a layout of the internal constituents of the probe according to one of the embodiments of the present invention.

In the configurations as illustrated in FIGS. 10A, 10B and FIGS. 11A, 11B, the emission light path L1 of the excited light and the incident light path L2 of the reflected light are inclined away from the direction normal to the axis of rotation X, towards the field of view Y of the imaging camera 9. In this way, even if the center of field of view YA inclines towards the probe end, the site based on the detection of fluorescent light may be brought into the field of view Y as illustrated in FIGS. 10A and 10B. Alternatively as illustrated in FIGS. 11A and 11B, the site based on the detection of fluorescent light may be brought with a time lag into the field of view Y, as the rotating unit M rotates. FIG. 12B is a schematic drawing of a layout of the constituents, by which the center of field of view YA is directed normal to the axis of rotation X, and the emission light path L1 of the excited light and the incident light path L2 of the reflected light are inclined towards the field of view Y. By adjusting the orientation of the mirror 8, the light path for the fluorescence observation may be inclined away from the normal direction so as to overlap the field of view of the camera.

Figure 12C:
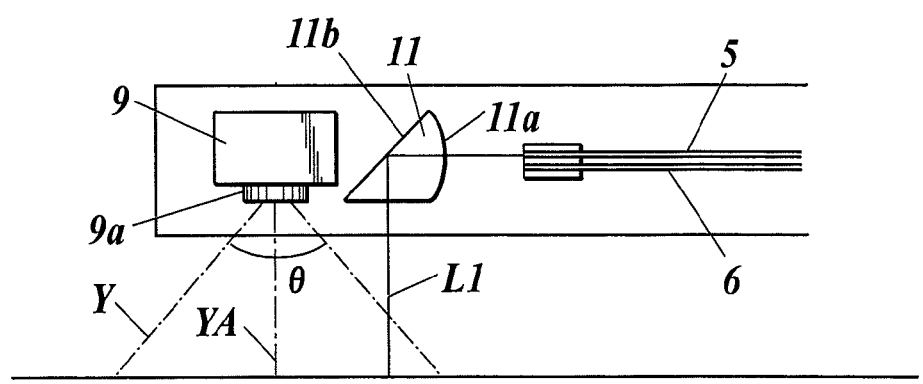
FIG. 12C is a schematic side elevation illustrating a layout of the internal constituents of the probe according to one of the embodiments of the present invention.

A configuration illustrated in FIG. 12C relates to an exemplary case of using an optical element 11 having a condensing surface 11a in place of the condenser lens 7, and a reflective surface 11b in place of the mirror 8.

Figure 13A:
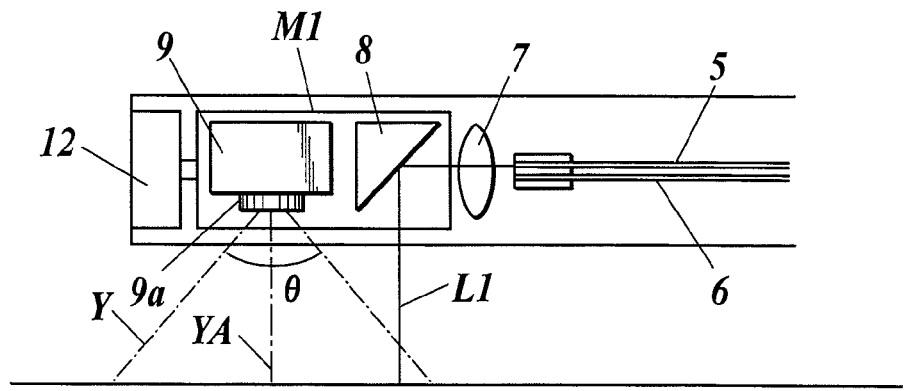
FIG. 13A is a schematic side elevation illustrating a layout of the internal constituents of the probe according to one of the embodiments of the present invention.
Figure 13B:
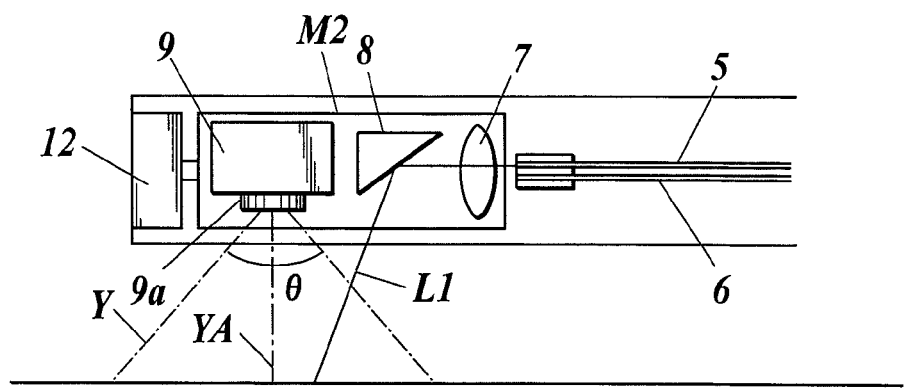
FIG. 13B is a schematic side elevation illustrating a layout of the internal constituents of the probe according to one of the embodiments of the present invention.
Figure 13C:
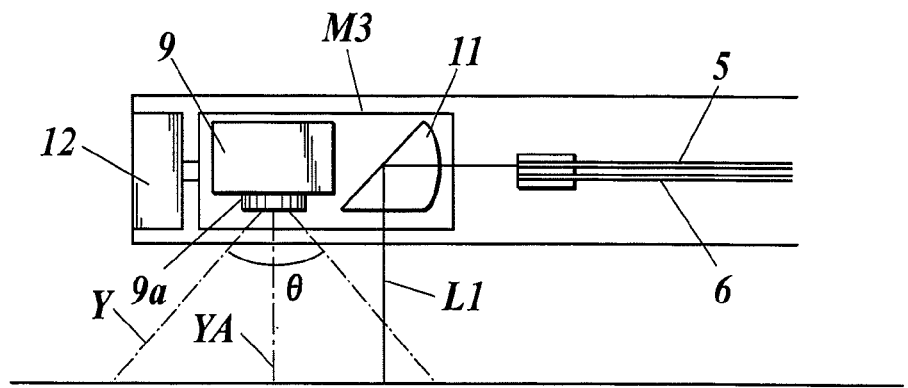
FIG. 13C is a schematic side elevation illustrating a layout of the internal constituents of the probe according to one of the embodiments of the present invention.

Least elements to be mounted on the rotating unit are the imaging camera 9, and the optical element which determines the direction of incidence of the reflected light to be received by the probe, or, the direction of observation of fluorescent light. Accordingly, there are various possible configurations including a rotating unit M1 having the mirror 8 and the imaging camera 9 as illustrated in FIG. 13A; a rotating unit M2 having the condenser lens 7 and the mirror 8 and the imaging camera 9 as illustrated in FIG. 13B; and a rotating unit M3 having the optical element 11 and the imaging camera 9 as illustrated in FIG. 13C. By connecting any one of these rotating units M1, M2 and M3, for example, to the output end of the servo motor 12 disposed on the probe end side, the rotational scanning may be implemented.

FIG. 12B illustrates a configuration in which the light path for fluorescence observation is inclined away from the camera for capturing image in the normal direction. By adopting a camera having a wider view angle, a window for fluorescence observation (for example, the entire portion of the window 4*b*) may be included in the field of view, and therefore foul adhesion may be monitored.

More specifically, it is effective to configure the field of view Y1 of the imaging camera 9 as indicated by the broken line in FIG. 12B, so as to contain a region Z1 on the outer surface of the probe where the excited light and the reflected light to be received pass through. In this case, foul on the outer surface, which would adversely affect the measurement of fluorescent light, becomes detectable, and this benefits maintenance of measurement accuracy.

All of the embodiments described in the above dealt with the case where the optical fibers are used for irradiating the excited light onto the site, and for receiving the fluorescent light caused by the excited light, the optical fibers may alternatively receive scattered light or Raman scattered light caused by the irradiated light. Also in these cases, state of disease in biological tissue such as degeneration and cancer may be diagnosed.

INDUSTRIAL APPLICABILITY

As described in the above, the probe of the present invention is adoptable to observation of biological tissue, for the purpose of medical diagnosis.

EXPLANATION OF THE MARKS 1 tube
1A torque tube
2 end sheath
3 torque coil
4 unit frame
4*a* unit frame base
4*b* window
5 irradiating optical fiber
6 receiving optical fiber
7 condenser lens
8 mirror (or prism)
9 imaging camera
10 outer tube
10*a* balloon
11 optical element
11*a* condensing surface
11*b* reflective surface
12 servo motor
L1 emission light path
L2 incident light path
M rotating unit
M1 rotating unit
M2 rotating unit
M3 rotating unit
X axis of rotation
Y field of view
Y1 field of view
YA center of field of view
Z1 region
θ view angle

The invention claimed is:
1. A probe comprising:
an optical system which irradiates a site of a biological tissue to be observed with irradiation light and receives emission light emitted from the site; and
an imaging camera which captures a surface image of the site,
wherein the imaging camera is disposed closer to an end of the probe than an entirety of the optical system,
wherein the imaging camera and the optical system are aligned in an axis of rotation which is directed to a longitudinal direction of the probe,
wherein the probe is configured to rotate a direction of incidence of the emission light to be received on the probe and a direction of imaging of the imaging camera around the axis of rotation while fixing an angle between the direction of incidence and the direction of imaging, and
wherein the optical system receives the emission light emitted from the site to be observed, which always falls in a field of view of the imaging camera, or brought with a time lag into the field of view of the imaging camera as a result of rotation, the emission light being incident on the probe in a direction normal to, or inclined away from, the axis of rotation.

2. The probe of claim 1, wherein the optical system comprises:
an irradiating optical fiber for irradiating the irradiation light;
a receiving optical fiber for receiving the emission light; and
an optical element disposed ahead of the irradiating optical fiber and the receiving optical fiber, closer to the end of the probe, and having a reflective surface in a light path of the emission light, so as to allow the receiving optical fiber to receive the emission light coming into the probe in the direction normal to, or inclined away from, the longitudinal direction of the probe.

3. The probe of claim 1, wherein the field of view of the imaging camera contains a direction normal to a direction pointed by the end of the probe.

4. The probe of claim 3, wherein the field of view of the imaging camera contains the direction pointed by the end of the probe.

5. The probe of claim 3, wherein the field of view of the imaging camera contains passageways of the irradiation light and the emission light on an outer surface of the probe.

6. The probe of claim 1, wherein the optical element which determines the direction of incidence of the emission light on the probe, and the imaging camera are attached to a unit, and
wherein the probe further comprises a rotating section rotating the unit around the axis of rotation.

7. The probe of claim 1, configured to receive the emission light emitted from the site to be observed, which always falls in the field of view of the imaging camera, or brought with a time lag into the field of view of the imaging camera as a result of rotation, by adjusting the direction of incidence more largely inclined towards the field of view of the imaging camera, away from the direction normal to the axis of rotation.

8. The probe of claim 1, configured to receive the emission light emitted from the site to be observed, which always falls outside the field of view of the imaging camera, and brought with a time lag into the field of view of the imaging camera as a result of rotation.

9. The probe of claim 8, configured to receive the emission light emitted from the site to be observed, which always falls outside the field of view of the imaging camera, and brought with a time lag into the field of view of the imaging camera as a result of rotation, by ensuring a relative angle to the view angle of the imaging camera between the direction of incidence and the axis of rotation.

10. The probe of claim 6, wherein the field of view of the imaging camera contains the direction normal to the axis of rotation.

11. The probe of claim 10, wherein the field of view of the imaging camera contains the direction pointed by the end of the probe.

12. The probe of claim 10, wherein the field of view of the imaging camera contains a region on an outer surface of the probe where the irradiation light and the emission light pass through.

13. The probe of claim 1, wherein the optical system receives fluorescent light, scattered light or Raman scattered light caused by the irradiation light.

* * * * *